United States Patent [19]

Kimball et al.

[11] 4,438,104

[45] * Mar. 20, 1984

[54] ENDORPHINS HAVING PLACENTAL OR PANCREATIC ORIGIN

[75] Inventors: Charles D. Kimball; John C. Houck, both of Seattle, Wash.

[73] Assignee: Endorphin, Inc., Seattle, Wash.

[*] Notice: The portion of the term of this patent subsequent to Feb. 23, 1999 has been disclaimed.

[21] Appl. No.: 394,340

[22] Filed: Jul. 1, 1982

Related U.S. Application Data

[63] Continuation-in-part of Ser. No. 293,118, Aug. 17, 1981, abandoned, which is a continuation of Ser. No. 109,233, Jan. 3, 1980, Pat. No. 4,316,895.

[51] Int. Cl.³ .................. A61K 37/00; C07C 103/52
[52] U.S. Cl. ........................... 424/177; 260/112.5 R
[58] Field of Search ................ 424/177; 260/112.5 R

[56] References Cited

U.S. PATENT DOCUMENTS

| | | | |
|---|---|---|---|
| 3,842,063 | 10/1974 | Chance et al. | 260/112.5 |
| 4,038,222 | 7/1977 | Li | 260/8 |
| 4,073,885 | 2/1978 | Pert et al. | 424/101 |
| 4,098,778 | 7/1978 | Li | 424/177 |
| 4,105,651 | 8/1978 | Hughes | 424/177 |
| 4,116,950 | 9/1978 | Li | 424/177 |
| 4,264,492 | 4/1981 | Stein | 424/177 |
| 4,316,895 | 2/1982 | Kimball et al. | 424/177 |

OTHER PUBLICATIONS

Gautray et al., "Presence of Immunoassayable β-Endorphin in Human Amniotic Fluid: Elevation in Cases of Fetal Distress", Am. J. Obst. Gynecol., 129, pp. 211–212 (1977).

Nakai et al., "Presence of Immunoreactive β-Lipotropin and β-Endorphin in Human Placenta", Life Sci., 23, pp. 2013–2018 (1979).

Kimball, "Do Endorphin Residues of Beta Lipotropin Hormone Reinforce Reproductive Functions?", Am. J. Obst. Gynecol., vol. 134, No. 2, pp. 127–132, (1979).

Pedigo et al., "Demonstration of Placental Endorhins by Radioimmunoassay and Radioreceptor Techniques", (1979).

Bruni et al., "β-Endorphin in the Human Pancreas", J. Clin Endocrin. and Metab., vol. 49, No. 4, pp. 649–651 (1979).

Houck et al., "Placental β-Endorphin–Like Peptides", Science, vol. 207 and pp. 78–80 (1980).

Snyder, "The Brain's own Opiates", C&EN, Nov. 28, 1977 pp. 26–35.

Fox, "Scientists Face Explosion of Brain Components", C&EN, Nov. 19, 1979, pp. 30—34.

Odagiri et al., "Human Placental Immunoreactive Corticotropin, Lipotropin, and β-Endorphin: Evidence for a Common Precursor", Proc. Natl. Acad. Sci., vol. 76, No. 4, pp. 2027–2031, (Apr. 1979).

Yang, "Characterization of High Molecular Weight Enkephalin like Materials in Adrenal Medulla", Federation of American Societies for Experimental Biology, 64th Annual, (614), (Apr. 13–18, 1980).

Hexum, "Secretion of Enkephalin–like Peptides from Dog Adrenal Gland", (1799) Federation of Americal Societies for Experimental Biology, 64th Annual Meeting (Apr. 13–18, 1980).

*Primary Examiner*—Delbert R. Phillips
*Attorney, Agent, or Firm*—David G. Conlin; George W. Neuner

[57] ABSTRACT

An endorphin peptide is described that has a molecular weight by amino acid analysis of about 14,000 daltons, an infrared spectrum substantially as shown in FIG. 5, and an amino acid analysis substantially as follows:

| Amino Acid | Nanomoles |
|---|---|
| Aspartic acid | 9.4 |
| Threonine | 6.2 |
| Serine | 10.1 |
| Glutamic acid | 16.0 |
| Proline | 6.3 |
| Glycine | 18.6 |
| Alanine | 12.5 |
| Valine | 6.0 |
| Methionine | 1.0 |
| Isoleucine | 2.6 |
| Leucine | 7.1 |
| Tyrosine | 1.1 |
| Phenylalanine | 4.3 |

| Amino Acid | Nanomoles |
|---|---|
| *-continued* | |
| Histidine | 3.6 |
| Lysine | 7.8 |
| Arginine | 2.8 |

| Amino Acid | Nanomoles |
|---|---|
| *-continued* | |
| Total | 115.4 |

The peptide is immunoreactive against $\beta$-endorfin rabbit antisera and displaces Naloxone from opiate receptors in brain tissue.

2 Claims, 6 Drawing Figures

ENDORPHINS HAVING PLACENTAL OR PANCREATIC ORIGIN

This application is a continuation-in-part of Ser. No. 293,118 filed Aug. 17, 1981 now abandoned which is a continuation of application Ser. No. 109,233 filed Jan. 3, 1980, now U.S. Pat. No. 4,316,895 issued 2/23/83.

FIELD OF THE INVENTION

This invention is related to endorphins such as beta-endorphin and enkephalin and particularly to an endorphin having a molecular weight substantially larger than beta-endorphin based on exclusion chromatography, having beta-endorphin-like activity, and which can be obtained from tissues of the placenta and the pancreas, as well as method of making and using such endorphins.

BACKGROUND OF THE INVENTION

Beta endorphin is an endogenous opioid peptide hormone released from the pituitary during stress having the same peptide sequence as the 61 to 91 portion of beta lipotropin. This peptide has been recognized as an endogenous morphine-like analgesic.

Guatray et al., Am. J. Obst. Gynecol. 129, 211 (1977) disclosed that amnionic fluid contains a significant amount of beta endorphin as detected by radioimmunoassay (RIA). Further, acid extracts of human placenta have been disclosed by Nakai et al., Life Sci., 23 2013 (1978) to contain both beta-endorphin and ACTH as well as beta lipotropin.

SUMMARY OF THE INVENTION

We have discovered a endorphin peptide (hereafter p-endorphin) having a molecular weight significantly greater than beta-endorphin that has beta-endorphin-like activity in radio-immunoassay against beta-endorphin rabbit antisera and in radio-receptor assay (RRA) against $H^3$-Naloxone in brain tissue. The p-endorphin also exhibits an analgesic effect in mammals. Unlike beta-endorphin, our endorphin peptide does not exhibit respiratory depressor effect when administered to mice.

P-endorphin, in accord with the present invention can be found in substantial quantities in or associated with placental and pancreatic tissue although it is apparently absent in a number of other tissues (including, for example, liver, lung, kidney, spleen and thymus. Preferably, the p-endorphin is extracted from tissue preparations by dilute mineral acid. The extract is then clarified, neutralized and incubated to denature proteolytic enzymes. The resulting product is then further purified by filtration.

Figure 5:
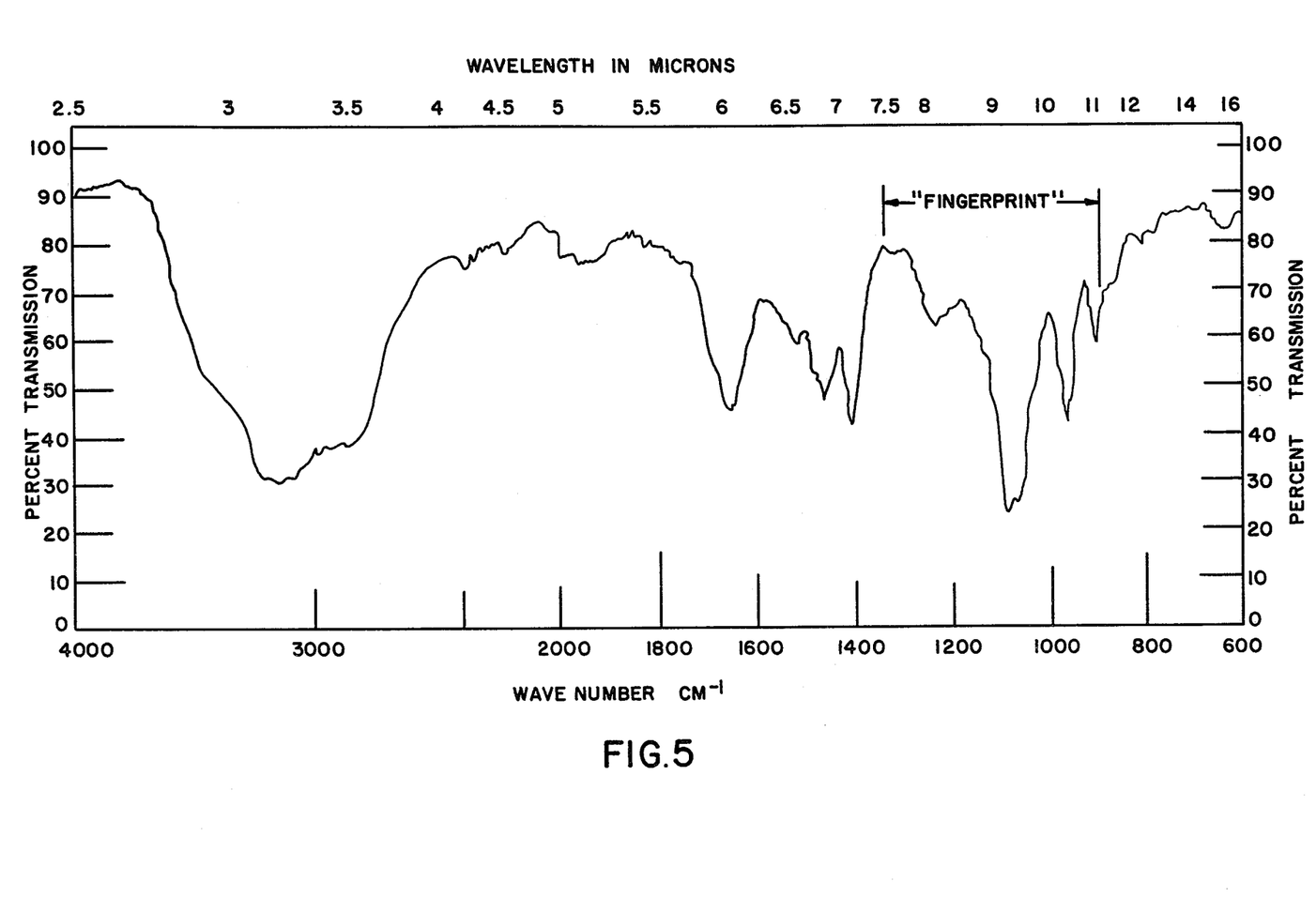
FIG. 5 is an infrared spectrograph of purified p-endorphin of the present invention prepared from pancreatic tissue in accord with an embodiment of this invention.

In one embodiment of the present invention, p-endorphin is provided having an infrared spectron as illustrated in FIG. 5 and an amino acid analysis as follows:

| Amino Acid | Nanomoles |
| --- | --- |
| Aspartic acid | 9.4 |
| Threonine | 6.2 |
| Serine | 10.1 |
| Glutamic acid | 16.0 |
| Proline | 6.3 |
| Glycine | 18.6 |
| Alanine | 12.5 |
| Valine | 6.0 |
| Methionine | 1.0 |
| Isoleucine | 2.6 |
| Leucine | 7.1 |
| Tyrosine | 1.1 |
| Phenylalanine | 4.3 |
| Histidine | 3.6 |
| Lysine | 7.8 |
| Arginine | 2.8 |
| Total | 115.4 |

Total molecular weight of the p-endorphin by amino acid analysis is approximately 14,000 D.

The p-endorphin of this invention is useful among other things for the therapeutic treatment of mental depression, opium and alcohol addiction, and geriatric disphoria.

DESCRIPTION OF THE INVENTION

In accord with the present invention p-endorphin preparations are prepared by extraction from placental and pancreatic tissue with dilute mineral acid. Placental tissue is preferably extracted directly with dilute mineral acid, for example 0.1 M HCl with a pH of 1.8. Because extracts of fresh bovine and porcine pancreas apparently do not contain p-endorphin when extracted by dilute mineral acid, it is preferred to prepare such pancreatic tissue by treating it with large volumes of acetone to form a powder. This acetone powder is then extracted with dilute mineral acid as above. Also found useful for extracting p-endorphin are commercial dessicated and defatted tissue powders prepared from pancreas by Viobin Corporation (Monticello, IL) including "Pancrelipase" which is similar extract of pork pancreas prepared using 1, 2-dichloroethanol.

Because p-endorphin is a peptide subject to proteolysis, it is preferable to extract it with dilute mineral acid. The extract is clarified by centrifugation, quickly neutalized and incubated, for example at 70° C. for 20 minutes, to denature both peptidases and proteases.

The resulting clarified supernatant can be further purified by, for example, hollow-fiber ultrafiltration and concentrated.

The beta-endorphin-like activity of p-endorphin molecules has been demonstrated utilizing and RIA test kit for beta-endorphin developed by the New England Nuclear Company, involving antisera from rabbits prepared against synthetic human beta endorphin synthesized by the Peptide Division of the Beckman Company, and utilizing an RRA involving the displacement of $H^3$-Naloxone from binding sites in the brain after extensive washing to eliminate contaminating peptidases. A crude placental extract in accord with this invention required 4.4 mg/ml to displace 50% $H^3$-Naloxone in the RRA.

The extracts of p-endorphin were also subjected to molecular exclusion chromatography. As a result of such exclusion chromatography it was concluded that the molecular weight of p-endorphin is in the range of about 4500 to 5000 daltons, i.e., approximately 4800 daltons and that this is equivalent to a peptide that comprises about 43 amino acid residues. However, based on amino acid analysis the molecular weight of p-endorphin from pancreatic tissue was calculated to be 14,000 daltons. Thus, the p-endorphin of our ivnention has a substantially higher molecular weight than the pituitary hormone.

The following examples are set forth to further illustrate the present invention. In the examples the following assays are used.

1. RADIOIMMUNOASSAY (RIA) PROCEDURE

The New England Nuclear Company has devised a RIA test kit for beta endorphin using antisera prepared in the rabbit against synthetic human beta endorphin. The procedures described in the instruction book involve removal of the free $^{125}I$-labeled synthetic beta endorphin antigen from that bound to the antibody with activated charcoal. This method is sensitive to a minimum of 2 picograms/ml of beta endorphin and is unreactive to both ACTH and enkephalin. The method has shown some cross-reactivity with beta lipotropin, however. Recovery experiments indicate approximately 80 to 85% recovery of snythetic beta endorphin from human plasma and we have found the normal circulating value in humans to be between 0 and 90 picograms/ml with an average of approximately 26 picograms. Internal standard deviation of replicate determinations would be approximately 11% of this mean value.

2. RADIORECEPTOR ASSAY (RRA) PROCEDURE

Binding of $H^3$-Naloxone (14.6 Ci/mole, New England Nuclear) was assayed in rat brain tissue in the absence of sodium ion. Fresh rat brain with the cerebellus removed was weighed and then homogenized in 40 ml ice cold Tris HCl buffer (0.05 M, pH 7.4). After centrifugation at 48,000×g for 10 min the pellet was re-suspended in 40 ml Tris buffer and the washing procedure repeated twice. The thrice washed pellet was finally re-homogenized in 9 volumes of Tris buffer. Aliquots of the tissue brei (final assay concentration 10 mg wet weight per ml), $H^3$-Haloxone (1.2 nM) and drugs or tissue extracts were incubated in Tris buffer (2 ml) for 2 hours at 0° C. in an ice water bath. The binding reaction was terminated by filtration through Watman GF/B filters which were rinsed four times with 5 ml ice-cold buffer. Radioactivity was extracted from the filters overnight in 6 ml scintillation fluor (prepared by mixing 2 l of Toluene with 1 l Triton X100 and 16 grams Omnifluor) and measured in a liquid scintillation counter. Control displacement curves for Naltrexone and Levorphanol were determined in each individual assay. Specific $H^3$-Naloxone binding was defined as the total binding in the absence of drugs minus the binding in the presence of 1 M Naltrexone or Levorphanol.

The binding of $H^3$-Naloxone to opiate receptors in rat brain homogenates was shown in these studies to be stereospecific as Levorphanol was 500 times more potent in displacing Naloxone than its biologically inactive enantiomer Dextrophan.

EXAMPLE 1

P-endorphin from Human Placenta

Human placenta was extracted with dilute mineral acid (0.1 M HCl, pH 1.8). This extract was clarified by centrifugation, quickly neutralized and incubated at 70° C. for 20 minutes to denature proteolytic enzymes including both peptiadases and proteases. We have separately shown than human placenta contains cathepsin D protease activity, maximally active at ph 3 and completely inhibited by pepstatin. The resulting clarified supernatent in turn was expressed through a 5,000 dalton hollow-fiber Amicon ultrafilter and concentrated over a 1,000 (UM-2) membrane filter. The retentate was assayed by RIA as well as by RRA and then lyophilized. The salt-free prepartion was then re-dissolved in elution buffer and subjected to molecular exclusion chromatography using Sephadex G-25. Of the total reactive material in three extracts each of three separate placenta, approximately 60% of the RIA activity passed through the 5,000 dalton ultrafilter. Of the 40 percent of RIA and RRA active material that did not pass through this filter, the vast majority (i.e. 85%) was found by Sephadex G-200 exclusion chromatography to be in a general weight range of between 25,000 and 50,000 daltons.

Figure 1:
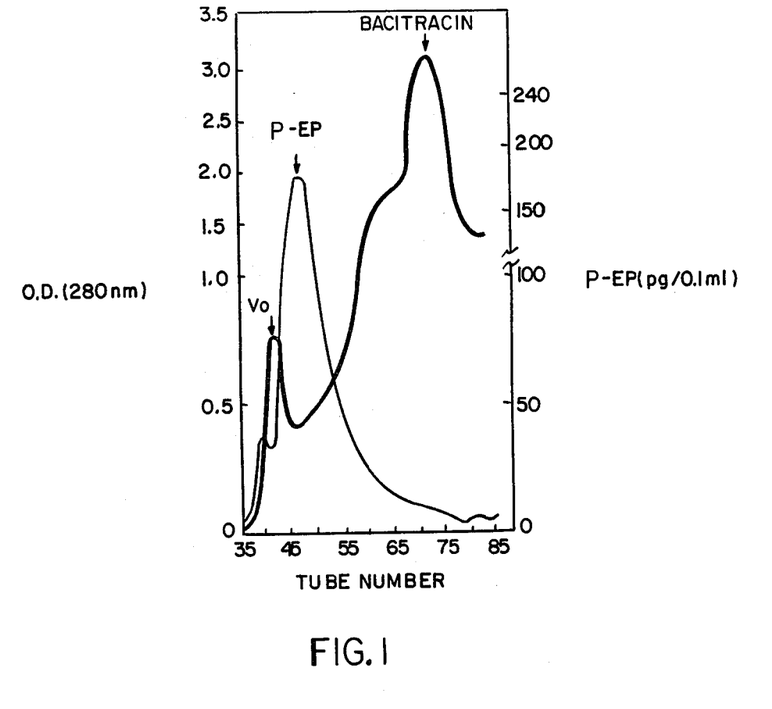
FIG. 1 is an illustration of the elution profile of a p-endorphin preparation prepared from placental tissue in accord with an embodiment of this invention.

The elution profile from the G-25 chromatography is illustrated in FIG. 1 in which RIA activity is compared with the 280 nm absorbance of the column eluate and the elution volume of both $^{125}I$-labelled suynthetic pituitary endorphin (3400 daltons) and bacitracin (1411 daltons) used as molecular size standards. The $^{125}I$-endorphin was also run on a G-25 column after being mixed with crude placented extract. The elution volume was the same as that demonstrated by pure standard.

The acid extract of the human placenta which passed through a 5,000 dalton ultrafilter, was chromatographed on a 2.5×90 cm column in 10 mM sodium acetate buffer pH 4.3 and 0.15 M NaCl. The absorbance at 280 nm (solid line, left ordinate) is compared with the immunoreactivity determined by RIA (shaded areas, right ordinate). The exclusion volume ($v_o$) was determined with bovine serum albumin (68,000 daltons) and the column standardized in addition by using bacitracin (1411) and by $^{125}I$-labelled synthetic human beta endorphin (3465).

The data of FIG. 1 indicate that approximately 75% of the RIA reactive p-endorphin is found in the void or exclusion volume of G-25. This is significantly larger than the standard $^{125}I$-labelled beta endorphin. Twenty percent or so of the total RIA activity that could be expressed through a 5,000 dalton ultra-filter was in a position between beta endorphin and bacitracin with a molecular weight of approximately 2200 daltons. This corresponds to gamma endorphin in size but gamma endorphin, which is released from beta endorphin by the proteolytic activity of cathepsin D and has the same sequence as the first 17 amino acids of beta endorphin, does not cross-react with beta endorphin antisera. Thus it may be that this is a fragment of p-endorphin which unlike gamma endorphin reacts with the antisera synthetic beta-endorphin.

Pools of the RIA-determined p-endorphin in the void volume, as well as the RIA-identifiable material in a molecular weight range of 2200 daltons were both tested for their ability to displace radioactive Naloxone from rat brain binding sites. These results indicated that approximately 80% of the total RIA activity that moved through the 5,000 dalton filter was in the void volume and approximately 20% was held back behind standard beta endorphin. This distribution and size were unaffected whether the columns were run a pH 7.5 or at 4.5. The elution profile of this material was also developed on a BIO-RAD P6 column which has an exclusion limit of 6,000 daltons. The results indicate that this RIA determined p-endorphin having beta endorphin-like activity was held back on the P6 column but behind the void volumn; i.e., it has a molecular weight of slightly less than 5,000 daltons.

Thus, by both RRA and RIA we have found that mineral acid extracts of human placenta contained two beta endorphin-like materials, most of which consisted of p-endorphin which has a molecular weight equivalent to approximately 12 more amino acids than the material characteristical extracted from the pituitary, i.e., beta-endorphin. The nature of the smaller molecular weight material (2200 daltons) is unclear, since despite its size it is unlikely to be immunologically gamma endorphin. It may represent a degradation product by various peptidases of the larger molecular weight precursor which still possesses both RRA and RIA ativity despite its relatively small size. Clearly, human placenta contains two endorphin peptides which differ markedly in their size from the classical pituitary-derived hormone.

EXAMPLE 2

P-endorphin from Bovine Pancreas

Acetone powders were prepared using 5 volumes of 100% acetone per gram of fresh wet weight tissue of minced calf pancreas. These powders were prepared at 4° C. and were washed twice so that the powder resulting was a constant dry weight.

Fifty grams of these acetone powders were extracted with 10 volumes of 0.1 M HCl in a Waring Blender and allowed to extract with stirring at 4° C. for approximately 30 minutes. After centrifugation in the cold at 15,000×G, the clear supernatant (pH 1.8) was collected, quickly neutralized to apprximately pH 7 with 0.5N Tris-base, centrifuged, and the supernatant heated in a 90° C. water bath to 70° C. for 20 minutes. No precipitate resulted during this process. The clear solution was then concentrated and dialyzed on an Amicon Diaflo 500 dalto ultrafilter (UM-05) and lyophilized.

The reconstituted material (1% w/v) was subjected to hollow fiber ultrafiltration using the 5,000 dalton Amicon Diaflo system (DC-2). The material which was retained above 5,000 daltons was lyophilized. The material which passed through the 5,000 dalton hollow fiber ultrafilter was concentrated and dialyzed over UM-05 ultrafilters. The larger molecular weight material was then subjected to molecular exclusion chromatography using G-200 Sephadex with 0.1 M Tris buffer (pH 7.5). The material which passed through the filter was subjected to molecular exclusion chromatography using G-25 Sephadex at pH 4.3 (0.01 M acetate buffer) in 0.15 M NaCl. The G-200 Sephadex column was standardized with bovine serum albumin (68,000), ovalbumin (48,000) and chymotrypsinogen (25,700). The G-25 was standardized by $^{125}$I-labeled beta endorphin (Beckman Peptide) both separately in buffer and mixed with the ultrafiltrated pancreatic extract, as well as with bacitracin (1415). The elution profile from these Sephadex columns was monitored at 280 nm in the usual fashion and fractions collect in 5 ml volumes. Every fourth or fifth tube was monitored by RIA assay.

Finally, a Bio-Rad P6 column for exclusion chromatography was also prepred. Elution profiles were determined in 0.1 M Tris buffer, pH 7.5. Unlike G-25 which has a exclusion volume of approximately 5,000 D, Bio-Rad P6 has an exclusion volume of about 6,000 D.

Approximately half of this RRA and RIA-determined endorphin activity would pass through the 5,000 dalton hollow fiber ultrafilter. Material which did not pass through the filter was concentrated by further ultrafiltration, lyophilized and subjected to G-200 Sephadex exclusion chromatography. The results of screening the eluted fractions from this column by RIA are compared with the elution profiles of standard protein in FIG. 2.

Figure 2:
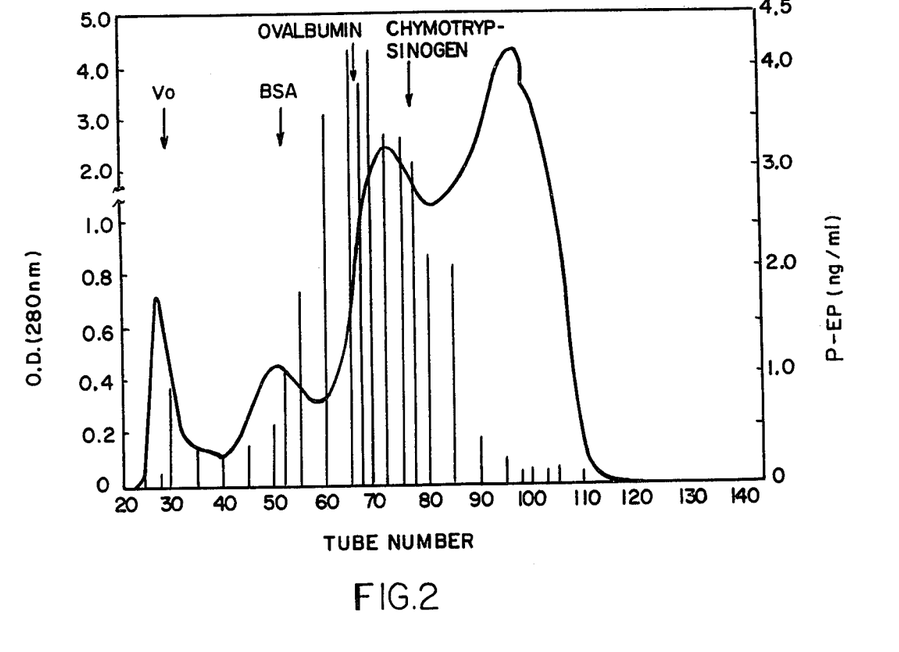
FIG. 2 is an illustration of the Sephadex G-200 elution profile and RIA beta-endorphin activity profile of a p-endorphin preparation prepared from pancreatic tissue in accord with an embodiment of this invention.

FIG. 2 illustrates the Sephadex G-200 elution profile and the RIA beta-endorphin activity profile. The materials that do not pass through a 5,000 dalton ultrafilter (384 mg/15 ml) were chromatographed on a 2.5×90 cm column and eluted with 0.1 M Tris-HC) buffer (pH 7.5) containing 0.02% sodium azide. The 280 nm absorbance (solid curved line, left ordinate) is compared with the RIA screening (straight lines, right ordiate) for beta endorphin immunoreactivity. Exclusion volume ($V_o$) was determined using blue Dextran 2000, and bovine serum albumin (BSA 68,000), ovalbumin (43,000 and chymotrypsinogen (25,700 were used to standardized the column.

Approximately 80 to 85% of all the activity by RIA was found in a molecular weight range approximately between 25,000 and 50,000 daltons. Very little RIA-determinable activity was found in the molecular weight range of normal pituitary beta-lipotropin (i.e. 10,000 daltons).

Figure 3:
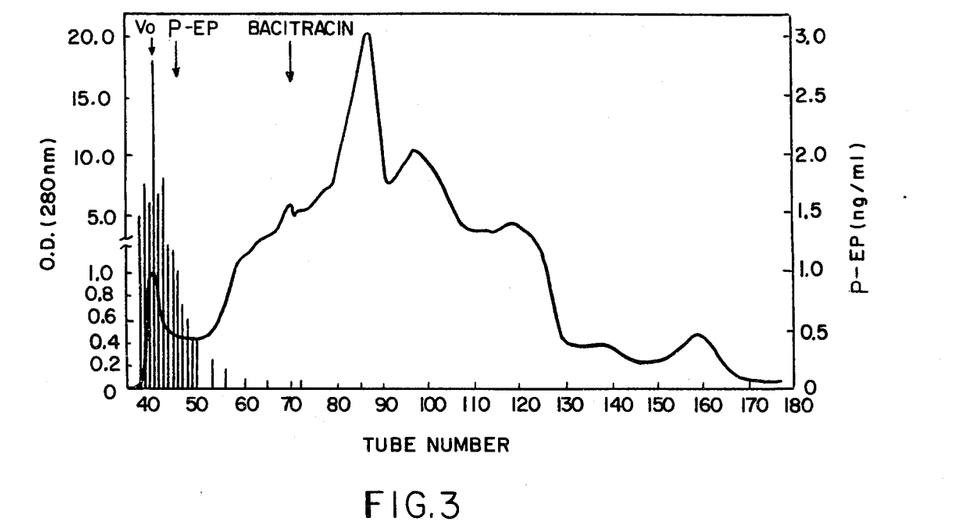
FIG. 3 is an illustration of the Sephadex G-25 elution profile and beta-endorphin immunoreactive profile of pancreatic extract having molecules with an apparent molecular weight less than 5,000 daltons.

The material having beta-endorphin-like activity which passed through 5,000 daltons was then subjected to G-25 Sephadex exclusion chromatography and the results are presented in FIG. 3.

FIG. 3 illustrates the Sephadex G-25 elution profile (280 nm, solid line, left ordinate) and beta-endorphin immunoreactive profile (straight line, right ordinate) of pancreatic extracts less than 5,000 daltons. 760 mg/10 ml was chromatographed on 2.5×90 cm column, eluted with 10 mM sodium acetate buffer (pH 4.3) cotaining 0.15 M NaCl. Exclusion volume was measured with bovine serum albumin (5,000 and up) and the column standards were bacitracin (1411) and radioactive human synthetic beta endorphin (3465) labeled with $^{125}$I. The position of elution of this labeled standard was not altered when mixed with pancreatic ultrafiltrate itself.

In FIG. 3, a comparison between the RIA screened elution profile and the UV-absorbing elution profile of p-endorphin is compared with that demonstrated for $^{125}$I-labeled synthetic beta endorphin, either in buffer solution or mixed with the tissue extract itself. In either case, its elution volume was unchanged and was distinctly less than that demonstrated by the "beta-endorphin-like" material which has passed through a 5,000 dalton hollow-fiber ultrafilter, and yet was still excluded on G-25 (exclusion volume is 5,000 daltons). None of the RIA determined p-endorphin from pancreas was found to be eluted from the column where the $^{125}$I-labeled synthetic pituitary endorphin was found.

Figure 4:
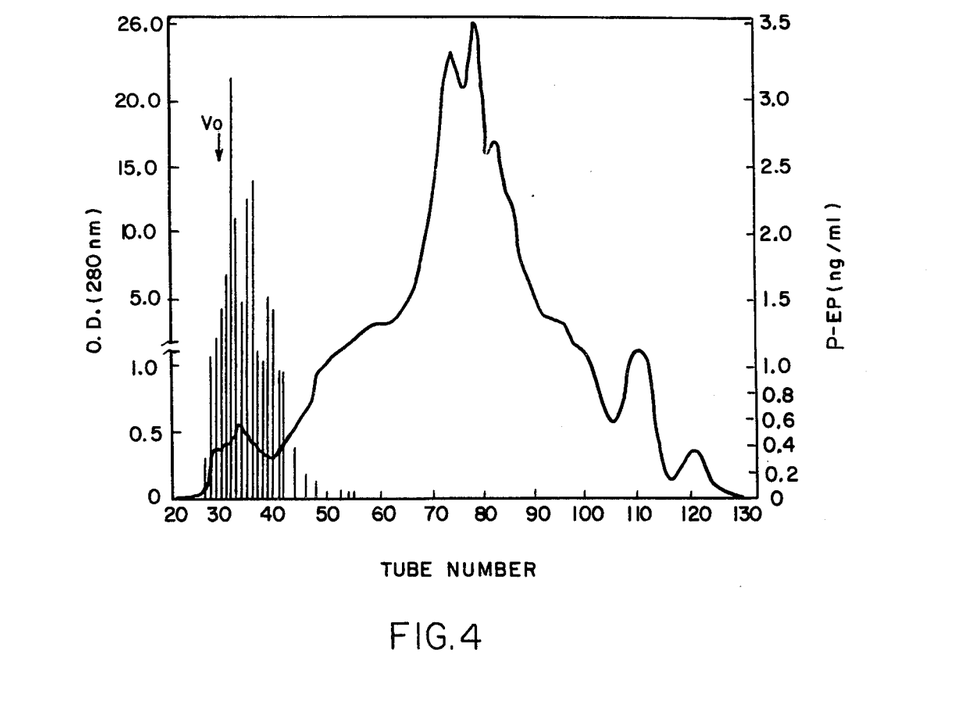
FIG. 4 is an illustration of the Bio-Gel P6 elution profile and the RIA beta-endorphin activity profile of pancreatic extract having molecules with an apparent molecular weight less than 5,000 daltons.

The void volume from G-25 was pooled, concentrated by ultrafiltration over a 500 dalton ultrafiltler and subjected to exclusion chromatography using Bio-Rad P6. As shown in FIG. 4, the RIA determined p-endorphin polypeptide was held 15 ml behind the void volume of this exclusion column.

FIG. 4 illustrates the elution profile of Bio-Gel P6 elution profile and the RIA of beta-endorphin profile.

Pancreatic extract of less than 5000 daltons (803 mg/10 ml) was chromatographed on a 2.5×90 cm column and eluted with 0.1 M Tris-HCl buffer, pH 7.5 in 0.02% sodium azide. 5.3 ml fractions were collected. Exclusion volume ($V_o$) was marked by bovine serum albumin. Beta-endorphin crossreactivity (straight lines) is expressed as ng/ml equivalents of RIA (left ordinate). Absorbance at 280 nm is the right ordinate.

The exclusion limit of P6 is approximately 6,000 daltons. Thus, it would appear that the p-endorphin having beta endorphin-like activity from acid extracts of pancreas acetone powders has a molecular weight slightly less than 5,000 daltons both by its movement through an ultrafilter and by its elution pattern from G-25 and separately from P6.

The p-endorphin obtained as in Example 2 was further purified and desalted using high pressure liquid chromotography (HPLC) using conventional techniques. About 20 to 50 mg of lyophilized P-EP ($NH_4H_2PO_4$) and injected into Perkin-Elmer HPLC system. (Series 3B solvent delivery system; Model LC-85, spectrophotometric detector autocontrol; Sigma 15, chromatography data station). The purification is achieved by utilizing reverse phase $C_{18}(10\mu)$ preparative column (25 cm×2.35 cm i.d.) with gradients of solvent A: 60% acetonitrile, $CH_3CN$ (Baker No. 3-9017) containing 0.05 M $NH_4H_2PO_4$ (Mallinckrodt No. 3272), $10^{-3}$M 2-mercaptoethanol (Mallinckrodt 1208) and solvent B: 0.05 M $NH_4H_2PO_4$. The millipore filtered and degassed solvents were pumped at room temperature, using 45-minute gradients from 6% to 60% $CH_3CN$ at a flow rate of 10 ml/min, 750 psig, back pressure. The major activity by both the RIA and analgesia by tail-flick in vivo assay of the mice was found at the elution peak of 30% $CH_3CN$; i.e. 50% of the gradient of solvent A. The procedure was repeated to desalt the P-EP for the amino acid sequencing procedure. An infrared spectrum was run obtaining the spectrograph illustrated in FIG. 5. Amino acid analysis of the purified p-endorphin yielded:

| Amino Acid | Nanomoles |
|---|---|
| Aspartic acid | 9.4 |
| Threonine | 6.2 |
| Serine | 10.1 |
| Glutamic acid | 16.0 |
| Proline | 6.3 |
| Glycine | 18.6 |
| Alanine | 12.5 |
| Valine | 6.0 |
| Methionine | 1.0 |
| Isoleucine | 2.6 |
| Leucine | 7.1 |
| Tyrosine | 1.1 |
| Phenylalanine | 4.3 |
| Histidine | 3.6 |
| Lysine | 7.8 |
| Arginine | 2.8 |
| Total | 115.4 |

Total molecular weight by amino acid is approximately 14,000 D.

EXAMPLE 3

Using p-endorphin as prepared in Example 2 tests of the delay in tail-flick in mice from a standardized heat injury were conducted under our direction and control as follows: Inbred mice (in this case Balb/C males weighing 20 to 25 gms) were held in a special body holder in cotton and a standardized "heat-run" or lamp was held a standardized distance away from the base of the tail which was painted black with india ink to increase the amount of energy it absorbs. On the average, 3.5 seconds of this heat is enough to cause these mice to flick their tail in a vigorous fashion. This end-point is unmistakable. The standard deviation of 50 determinations of this kind is approximately 0.7 seconds. Therefore, the normal range of large numbers of these mice with multiple determinations would be about 2.2 to 4.8 seconds. Thus, any delay longer than 5 seconds is more than two standard deviations higher than the mean and hence would be said to be statistically significant.

The data set forth below in Table 1 illustrate the amount of time for the onset of tail flicking by mice tested at various times after the injection of 0, 15, 30 or 60 g of p-endorphin (P-EP).

P-EP as well as standarized beta-endorphin and synthetic enkephalinamide all demonstrate a delay of more than 10 seconds in this assay.

TABLE 1

| | Effects of P-EP on Tail Flick Time Concentration/mouse, P-EP (G-50 peak 1 pool) | | | | | | | |
|---|---|---|---|---|---|---|---|---|
| Time | 0 μg | | 15 μg | | 30 μg | | 60 μg | |
| Min. | A. | B. | A. | B. | A. | B. | A. | B. |
| 2 | 1.6 sec. | 4.1 sec, | 4.1 sec. | 5.0 sec* | >10 sec* | >10 sec* | >10 sec* | >10 sec* |
| 4 | 2.4 | 3.7 | 3.3 | 3.7 | >10* | >10* | >10* | >10* |
| 6 | 1.4 | 4.9 | 4.8 | 3.4 | >10* | >10* | >10* | >10* |
| 8 | 2.6 | 4.1 | 4.4 | 3.4 | — | 6.0* | 8.9* | 8.4* |
| 10 | 2.6 | 5.0* | 4.1 | 4.0 | 8.0* | — | 8.0* | 7.2* |
| 12 | — | — | — | — | 7.4* | 6.0* | 7.0* | 7.2* |
| 14 | — | — | — | — | 7.0* | 5.8* | 3.8 | 7.2* |

The inhibition or delay in tail-flick caused by P-EP is overcome by Naloxone thus indicating interaction of the P-EP with the morphine binding sites of the brain.

From UV absorbance characteristics we concluded that the P-EP preparation used in these tests contains about 10% pure P-EP. Therefore, 30 μg of preparation would contain 3 μg of pure P-EP which is less than 0.5 nanamole. Beta-endorphine requires about 0.8 nanamoles per mouse to obtain the same in vivo effect.

In addition, as in the case of morphine, a 30 μg dose of P-EP when administered intraventricularly in 20 gm mice causes erection of the tail to a perpendicular position, a characteristic referred to as the "Staub tail". Most mice will respond to such a 30 μg dose of P-EP with a Staub tail, which is also characteristic of morphine and beta-endorphin. These behavioral end-points demonstrated by the tail-flick assay and Staub tail test along with the immunological and opiate receptor assay results show that the P-EP has utilities similar to morphine and beta-endorphin.

EXAMPLE 4

Isoelectric focusing was done to determine the isoelectric point of the activity using LKB ampholine preparative isoelectric focusing device in a sucrose gradient. Various fractions of p-endorphin prepared as in Example 2 were recovered in a pH gradient from essentially pH 3.5 to pH 10 and each of these fractions was then concentrated over an Amicon Diaflo filter (molecular weight size of 1,000 dalton). These fractions (11 of them) were individually desalted by G-50 Sephadex and assayed at different concentrations by intraventricular injection into mice. The major activity (P-EP) had an isoelectric point between 7 and 8.2. This material was extremely long-lasting; much longer acting in fact that the initial starting material as judged by both the tranquility of the animal and the delay in tail-flick assay. In addition, a narrow fraction ranging from 6.2 to 6.4 was also found to have activity. The primary product, however, was the material found in the isoelectric point range of approximately 7 to 8.2

EXAMPLE 5

Figure 6:
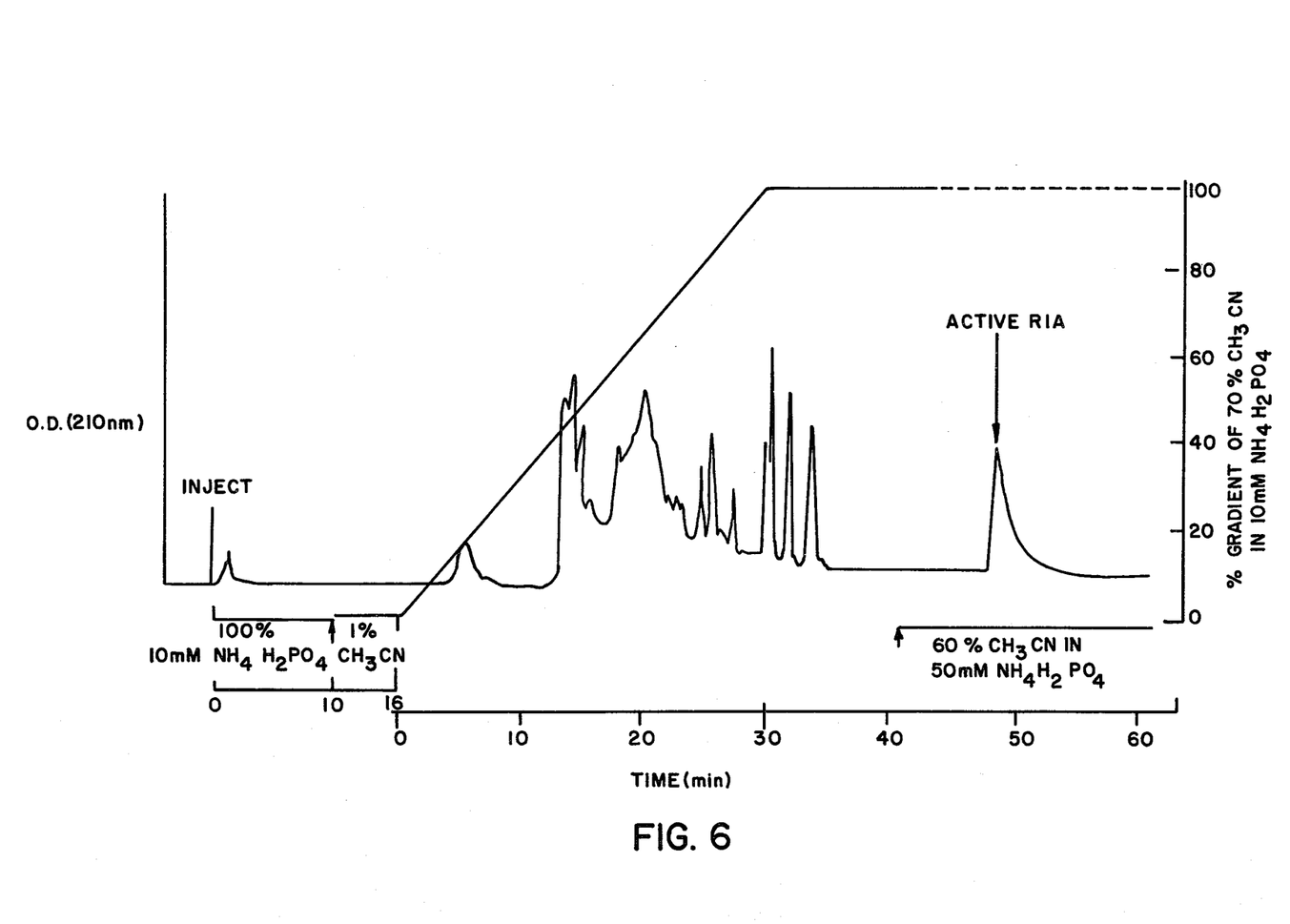
FIG. 6 is an illustration of a p-endorphin preparation in accord with this invention HPLC using 10 mM ammonium phosphate and an acetonitrile gradient.

P-endorphin obtained as described in Example 2 was run on high performance liquid chromatography in a Waters system using 10 mM ammonium phosphate as a salt solvent and developing a gradient of acetonitrile running from 0 to 70%. Essentially most of the material that was added into this system was eluted successfully as judged by absorbance in the UV; however, practically none of the endorphin-like activity (P-EP) was eluted from the column over this gradient. When 50 mM ammonium phosphate was used as a salt solvent together with 60% acetonitrile, all of the activity was eluted in a single peak. Since this column of reverse-phase C-8 is well known and well standardized, this constitutes a further major characteristic of the molecule in addition to its isoelectric point and its molecular size (i.e. that it is not eluted at low ionic strength from HPLC in acetonitrile gradient but it requires a higher ionic strength in the same amount of low water, i.e. 60% acetonitrile). This type of performance and its elution profile as indicated in FIG. 6 are characteristic of the molecule of P-EP.

Because approximately $10^{-8}$ M solutions of purified p-endorphin lead to a 50% displacement of the $H^3$-Naloxone, we calculate that by RRA approximately 50 times more material, or 2.5 g can be found per gram of acetone powder. This extreme difference between RIA and RRA for tissue-extracted beta endorphin activity was also found in placenta. Using the RRA assay, no other tissue extracts demonstrated any significant amounts of beta endorphin-like activity except those prepared from either placenta or pancreas.

The p-endorphin of this invention also has analgesic properties as determined by the rat "tail flick" test.

Because of its optiate receptor activity and other properties, the p-endorphin of this invention can be used for the therapeutic treatment of mental depression, opium and alcoholic addiction, and geriatric disphoria.

For each of these utilities the amount required of p-endorphin (hereafter referred to as the active ingredient) varies with the route of administration and with the severity of the condition to be treated, and ultimately is at the discretion of the physician or veterinarian. In general, however, for each of these utilities the dosage will be in the range of about 1.0 g. to 0.3 mg. per kilogram body-weight of mammal, and preferably about 10 g. to 0.1 mg./kg., (all dosages calculated with reference to the peptide base).

The active ingredients may be administered by any route appropriate to the condition to be treated, suitable routes including oral and parenteral (including subcutaneous, intramuscular and intravenous). It will be appreciated that the preferred route will vary with the condition to be treated.

While it is possible for the active ingredient to be administered as the raw chemical it is preferable to present it as a pharmaceutical formulation preparation.

The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and note deleterious to the recipient thereof. Desirably the formulation should not include oxidizing agents and other substances with which peptides are known to be incompatible.

The formulations include those suitable for oral or parenteral (including subcutaneous, intramuscular and intravenous, administrations, although the most suitable route in any given case will depend upon for example, the active ingredient and the condition to be treated. The formulations may conveniently be presented in unit dosage form and may be prepard by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a nonaqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations suitable for parenteral administration conveniently comprise sterile aqueous solutions of the active ingredient which solutions are preferably isotonic with the blood of the recipient. Such formulations may be conveniently prepared by dissolving solid active ingredient in water to produce an aqueous solution, and rendering said solution sterile may be presented in unit—or in multi-dose containers, for example sealed ampoules or vials.

It should be understood that in addition to the aforementioned ingredients the formulations of this invention may include on or more additional ingredients such as diluents, buffers, flavouring agents, binders, surface active agents, thickeners, lubricants, preservative (including anti-oxidants) and the like.

Where the formulation, for human or for veterinary use, if presented in unit dosage form, for example those unit dosage forms specifically mentioned above, each unit thereof conveniently contains the active ingredient (as above defined) in an amount in the range of about 0.5 to about 0.10 mg (all weights calculated with reference to the peptide base).

We claim:

1. An endorphin peptide having a molecular weight by amino acid analysis of about 14,000 daltons, having an infrared spectrum substantially as shown in FIG. 5, and having an amino acid analysis substantially as follows:

| Amino Acid | Nanomoles |
| --- | --- |
| Aspartic acid | 9.4 |
| Threonine | 6.2 |
| Serine | 10.1 |
| Glutamic acid | 16.0 |
| Proline | 6.3 |
| Glycine | 18.6 |
| Alanine | 12.5 |
| Valine | 6.0 |
| Methionine | 1.0 |
| Isoleucine | 2.6 |
| Leucine | 7.1 |
| Tyrosine | 1.1 |
| Phenylalanine | 4.3 |
| Histidine | 3.6 |
| Lysine | 7.8 |
| Arginine | 2.8 |
| Total | 115.4 | said peptide being immunoreactive against beta-endorphin rabbit antisera and displacing Naloxone from opiate receptors in brain tissue.

2. A pharmaceutical preparation useful for therepeutic treatment of mental depression, opium addiction, alcoholic addiction and geriatric disphoria said preparation comprisng effective amount of the endorphin peptide of claim 1 in a pharmacological carrier.

* * * * *